(12) United States Patent
Hosomi et al.

(10) Patent No.: US 7,450,789 B2
(45) Date of Patent: Nov. 11, 2008

(54) MICRO SENSOR DEVICE

(75) Inventors: Kazuhiko Hosomi, Tachikawa (JP); Hiroji Yamada, Harajuku 4-17-2, Shiroyama-machi, Tsukui-gun, Kanagawa, 220-1020 (JP); Toshio Katsuyama, Amagase, 1033-1-205, Oume-city, Tokyo, 198-0087 (JP); Yasuhiko Arakawa, Kami-asao 4-36-12, Asao-ku, Kawasaki-city, Kanagawa, 215-0021 (JP); Toshihiko Fukamachi, Kokubunji (JP)

(73) Assignees: Hitachi, Ltd., Tokyo (JP); Hiroji Yamada, Kanagawa (JP); Toshio Katsuyama, Tokyo (JP); Yasuhiko Arakawa, Kanagawa (JP)

( * ) Notice: Subject to any disclaimer, the term of this patent is extended or adjusted under 35 U.S.C. 154(b) by 0 days.

(21) Appl. No.: 11/485,294

(22) Filed: Jul. 13, 2006

(65) Prior Publication Data
US 2007/0014505 A1     Jan. 18, 2007

(30) Foreign Application Priority Data
Jul. 13, 2005    (JP)    ............................. 2005-203967

(51) Int. Cl.
*G02B 6/00* (2006.01)
(52) U.S. Cl. ....................................................... 385/12
(58) Field of Classification Search ........................ None
See application file for complete search history.

(56) References Cited

U.S. PATENT DOCUMENTS 5,859,893 A * 1/1999 Moorman et al. ............ 378/154
2002/0097947 A1 * 7/2002 Lim et al. ...................... 385/12
2004/0069948 A1 * 4/2004 Feisst et al. ................... 250/343
2005/0110992 A1 * 5/2005 Scherer et al. ................ 356/318

FOREIGN PATENT DOCUMENTS

JP    02-040537    2/1990
JP    07-198604    8/1995

OTHER PUBLICATIONS http://www.biacore.co.jp/3_1_3. shtml, May 9, 2005.
E. Chow et al., Ultracompact biochemical sensor built with two-dimensional photonic crystal, Optics Letters vol. 29, No. 10, p. 1093-1095 (2004).

* cited by examiner

*Primary Examiner*—Sung Pak
*Assistant Examiner*—Hoang Tran
(74) *Attorney, Agent, or Firm*—Antonelli, Terry, Stout & Kraus, LLP.

(57) ABSTRACT

The present invention provides an ultra-mini and low cost refractive index measuring device applicable to biochemical measurements of an extremely minute amount of a sample. The refractive index measuring device uses a photonic crystal without any requirement of an external spectrograph or the like.

The micro sensor device according to the present invention includes a light source emitting light with a single wavelength, a microcavity in which a resonant wavelength varies depending on a position thereof. A refractive index of a material to be measured is measured based on positional information by detecting a transmitting position of light changing in response to a change of a refractive index of the measured material. The micro sensor device according to the present invention enables measurement of a refractive index of a material to be measured without using a large-scale spectrograph.

6 Claims, 13 Drawing Sheets

US 7,450,789 B2

MICRO SENSOR DEVICE

CLAIM OF PRIORITY

The present application claims priority from Japanese application JP 2005-203967 filed on Jul. 13, 2005, the content of which is hereby incorporated by reference into this application.

FIELD OF THE INVENTION

The present invention relates to a structure of a micro sensor device which is applicable for biochemical measurement or other chemical measurements and is also capable of measurement of a refractive index of a minute amount of liquid, and to a method of manufacturing the micro sensor device and a method of applying the micro sensor device.

BACKGROUND OF THE INVENTION

It is required in the fields of biochemistry and medical measurements to measure low molecular-weight molecules such as glucose, ions, cell communication molecules, and peptides, and high molecular-weight molecules such as hormones, proteins and DNAs. In the biochemical measurements as described above, generally a quantity of samples is small, and a method is required for obtaining as much information as possible with a possibly minimum quantity of samples because minimally invasive checking is required.

As a means for measurement, a method is utilized in which a pair of molecules specifically binding to each other such as a pair of an antigen and an antibody, a pair of DNS sequences complimentary to each other, and a pair of a ligand and a receptor are used and one of the molecules in each pair is detected. In most of the cases, an analyte is detected by labeling a sample with a fluorescent material or a radioactive material and detecting the luminescence or the radioactivity. However, the method for using a label has the following problems relating to a process of labeling an analyte: (1) a sample is required to be diluted; (2) it takes time; (3) an activity of an analyte changes; and (4) specificity of an analyte changes. Therefore, a method for using a label has been sought. As described above, the biochemical measurement requires a method in which a sample required for measurement is minimal and labeling is not required.

Examples of the prior art-based technique for biochemical measurement utilizing specific binding of molecules and not requiring labeling include the method utilizing the surface plasmon resonance as disclosed, for instance, in "SPR DETECTION SYSTEM MEDIUM A" (online), Basic Principle of Technology, disclosed on a website of Biacore (searched on Jun. 13, 2005), <http://www.biacore, co.jp/3_1_3.shtml> searched on Jun. 13, 2006). A principle of this method is illustrated in FIGS. 1A to 1C. In the method cited above, as illustrated in FIG. 1A, one of a pair of molecules specifically binding to each other is fixed to an Au film on a surface of a sensor chip in advance. When an analyte is allowed to flow into a flow cell, the measuring objective molecules bond with the fixed molecules as illustrated in FIG. 1A. When such binding occurs, a refractive factor becomes larger locally at a place where the binding occurs. The change of the refractive index is detected through the surface plasmon. When light is directed to a face of the Au thin film opposite to the face to which the one of the molecules is fixed, the surface plasmon is excited under specific conditions. However, under the condition allowing for excitation of the surface plasmon, intensity of reflected light becomes lower. When a refractive index changes, the conditions allowing for excitation of the surface plasmon also change, and an angle at which intensity of the reflected light becomes lower change as shown in FIG. 1B. (The change is illustrated with the reflection light I and II in FIG. 1B). FIG. 1C illustrates that a change of the reflection light can be detected as a signal indicating a change of time during which the sample is allowed to flow in a flow cell. Therefore, by measuring angular distributions of intensities of the reflection light, a change of the refractive factor on the surface, namely, binding between one of the pair of the molecules specifically binding with the analyte in the sample can be detected. The principle of this method is based on detection of binding between biological molecules with high sensitivity by detecting a change of a refractive index on a surface of a sample via the surface plasmon phenomenon. However, the method of measuring a change of a refractive index by making use of the surface plasmon phenomenon has some problems in that the optical system inevitably becomes relatively larger with the cost high, in that the size reduction is difficult, and in that there is a limit in reducing a quantity of a sample to be measured.

A method using a photonic crystal has been studied on a technique enabling measurement of a refractive index with a minute amount of a sample. Examples of a method for measuring a refractive index using a photonic crystal include, for instance, a method described in OPTICS LETTER, Vol. 29, page 1093. A principle of the refractive index measurement using a photonic crystal described in the cited reference is now described below. The photonic crystal is a multi-dimensional periodic structure combining two or more mediums with different refractive indexes at a period of wavelength order. In the photonic crystal as described above, there is a wavelength range where light cannot propagate in the photonic crystal, namely, a frequency band called a photonic band gap. For instance, when light having a wavelength corresponding to the band gap is directed from outside to a photonic crystal, the light is completely reflected on the surface of the crystal because the light cannot be propagated inside of the crystal.

FIG. 2 illustrates a state in which a two-dimensional photonic crystal with a band gap is configured by piercing round holes in a shape of a triangular lattice on an SOI (silicon on insulator of a $SiO_2$ substrate), and light is confined when a point defect, namely a non uniformity defect is provided in the periodic structure. Since the periodic structure is disturbed at a point defect, even light having a wavelength in the band gap can be present. However, since there is not defect around the point defect in the photonic crystal, the light can not propagate to outside, and is reflected and confined within the point defect. That is to say, the photonic crystal at and around a point defect forms a microcavity, and light having a specific wavelength is firmly confined therein in the steady state (referred to as resonant mode).

When light is introduced into the photonic crystal microcavity as illustrated in FIG. 2, only light having a wavelength corresponding to the resonant mode passes through the resonator to form a sharp peak as shown in FIG. 3. In other words, only the light having a specific wavelength passes through the resonator and the light having other wavelengths is reflected. The wavelength at the resonant peak varies depending on, for instance, a refractive index of a substance forming the photonic crystal at and around the point defect.

FIG. 4 illustrates a spectrum described in OPTICS LETTER, vol. 29, page 1093. FIG. 4 shows changes of spectrum, in a case where liquid is injected into a round hole on a two-dimensional photonic crystal with a point defect as shown in FIG. 2, when a refractive index n of the liquid is changed to 1.446, 1.448, 1.450, 1.452, and 1.454. As illustrated in FIG. 4, a peak of the spectrum changes in correspondence to a very small change of the refractive index of the liquid, and it is understood that the refractive index can be detected by measuring the peak wavelength. In this figure, the two dimensional photonic crystal is shown by way of example. However, the same effect can be obtained also by using a one-dimensional photonic crystal having a structure in which two different layers with different refractive indexes are superimposed alternately, or a three-dimensional photonic crystal having a structure in which a periodic structure is three-dimensional if liquid serving as a sample can be introduced into the photonic crystal structure.

It is possible to build a resonator without using a photonic crystal. A photonic crystal resonator has the feature in which a size of the resonator is as very small as of wavelength order. Therefore, it is possible to detect a refractive index with a minute quantity of a sample. As described above, the photonic crystal microcavity allows for use of a minimal quantity of a sample for biochemical measurement. In addition, a detector having a micro detection area provides the possibility of integration of sensors and measurement at an atomic size level.

SUMMARY OF THE INVENTION

In the refractive index measuring method using the photonic crystal microcavity as described above, a refractive index is determined by a wavelength in the resonant mode. However, a light source having a broad band and a spectral device such as a diffraction grating are required, which inevitably leads to scaling up of a whole system. Besides, the cost is high since a number of component parts are required.

In order to solve the problems described above, an object of the present invention is to provide a ultra mini-size and low cost refractive index measuring device capable of measuring an extremely small amount of a sample using a photonic crystal and not requiring any external spectrograph.

A means for solving the problems in the conventional methods is described below with reference to FIGS. 5A to 5C.

An example illustrated in FIG. 5A is configured of light having a wavelength $\lambda_0$, three units of one-dimensional photonic crystal microcavities $1_A$, $1_B$ and $1_C$ having different sizes of defects and receiving the light, and a detector array including photo detectors $2_A$, $2_B$ and $2_C$ detecting light passing through the microcavities $1_A$, $1_B$ and $1_C$, respectively. The photonic crystal portion of each microcavity, for example, is configured of a plurality of thin plates formed from a Si substrate through semiconductor processes to each have a predetermined thickness and to be spaced apart from each other at a predetermined interval, and a thin plate having intermediate portions with different thicknesses. In addition, a space between the thin plates is filled with liquid of a substance having a refractive index of n.

A left-hand portion of FIG. 5B illustrates characteristics of the photonic crystal portion of each microcavity when a refractive index of the liquid of the measured substance is $n_1$. When the refractive index is $n_1$, a peak of a transmission spectrum of the photonic crystal of the one-dimensional photonic crystal microcavity $1_A$ coincides with the wavelength $\lambda_0$. However, peaks of transmission spectrum of the other one-dimensional photonic crystal microcavities $1_B$ and $1_C$ do not coincide with the wavelength $\lambda_0$. As a result, as illustrated in a right-hand portion of FIG. 5B, when light having a wavelength $\lambda_0$ is directed from outside with the liquid of the measured substance having a refractive index $n_1$ being filled therein, the light directed to the one-dimensional photonic crystal microcavity $1_A$ passes therethrough, and is detected by the photo detector device $2_A$. On the other hand, the light directed to the other one-dimensional photonic crystal microcavities $1_B$ and $1_C$ are reflected by the photonic crystals, so that it do not reach the photo detector devices $2_B$ and $2_C$. Therefore, only the photo detector device $2_A$ associated with the one-dimensional photonic crystal microcavity $1_A$ reacts.

On the other hand, FIG. 5C illustrates characteristics of a portion of a photonic crystal in each microcavity when a refractive index of liquid of measured substance is $n_2$. In association with a change of the refractive index of the liquid as a measured substance, the spectrums of the photonic crystals in the one-dimensional photonic crystal microcavities $1_A$, $1_B$ and $1_C$ also change. In this case, as shown by the transmission spectrums in a left-hand portion of FIG. 5C, a peak of the transmission spectrum of the photonic crystal of the one-dimensional photonic crystal microcavity $1_B$ coincides with the wavelength $\lambda_0$. Therefore, as illustrated in a right-hand portion of FIG. 5C, only the photo detector device $2_B$ associated with the one-dimensional photonic crystal microcavity $1_B$ reacts.

Hence, when liquid having an unknown refractive index is filled and measured in refractive index, it can be determined that, when the photo detector device $2_A$ reacts, the unknown refractive index of the liquid is $n_1$, and when the photo detector device $2_B$ reacts, the unknown refractive index of the liquid is $n_2$.

As described above, in the present invention, information on a refractive index of liquid as a measured substance can be obtained without using a spectrograph, because a change of the refractive index of the liquid is converted to positional information and then detected.

Although only the concept is illustrated in FIGS. 5A, 5B and 5C, needless to say, necessary frequency bands and resolutions should be obtained by making optimal designs concerning such parameters as a structure of an individual photonic crystal or the number of arrays according to conditions required in each measuring system.

As described above, the present invention can provide an ultra mini-size and low cost refractive index measuring device capable of measuring an extremely small amount of a sample using a photonic crystal and not requiring any external spectrograph, and of being applicable to biochemical measurement or the like.

DESCRIPTION OF THE PREFERRED EMBODIMENTS

First Embodiment

Figure 6A:
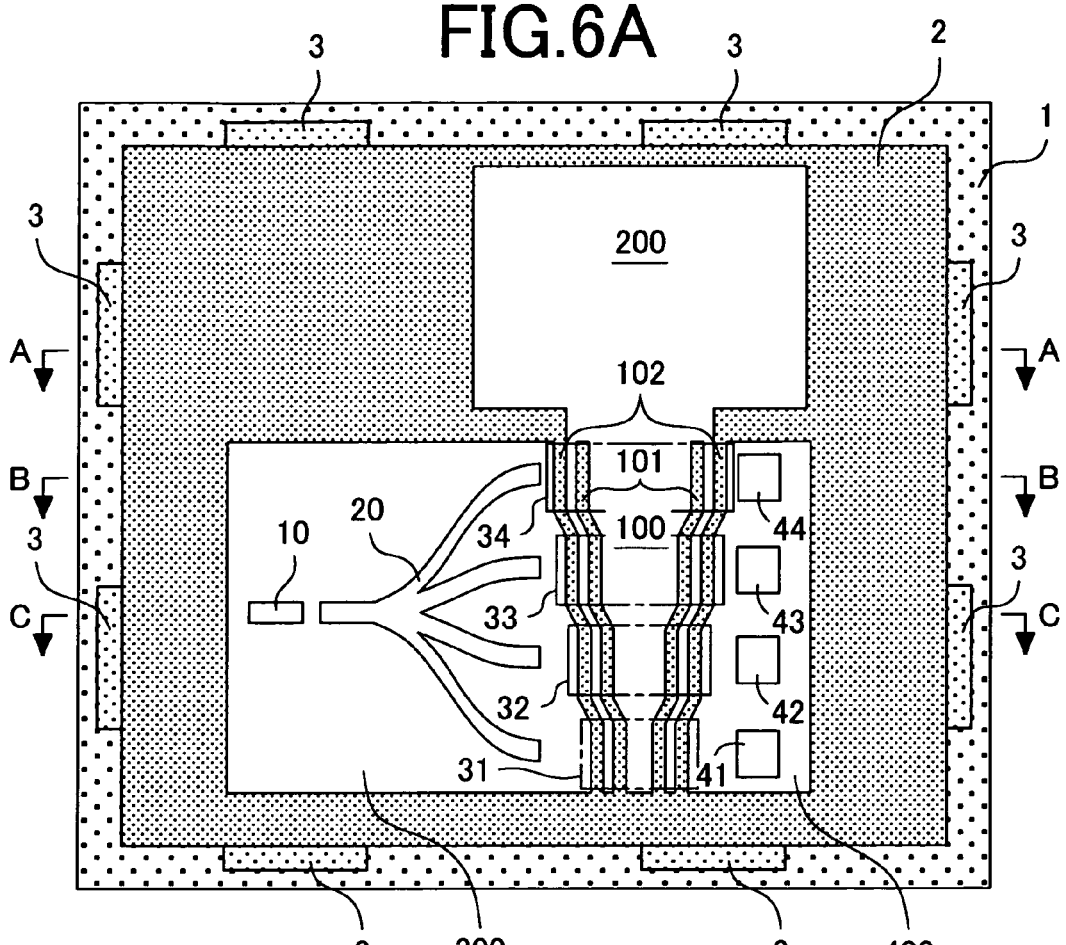
FIGS. 6A to 6D illustrate a micro sensor device according to a first embodiment of the present invention.
Figure 6B:
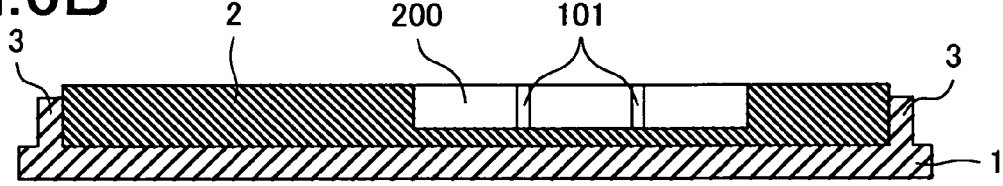
Figure 6C:
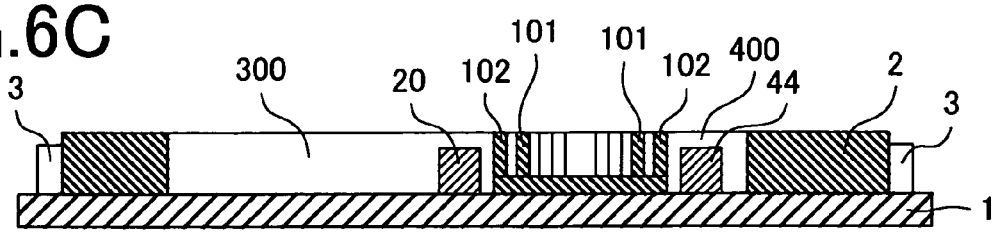
Figure 6D:
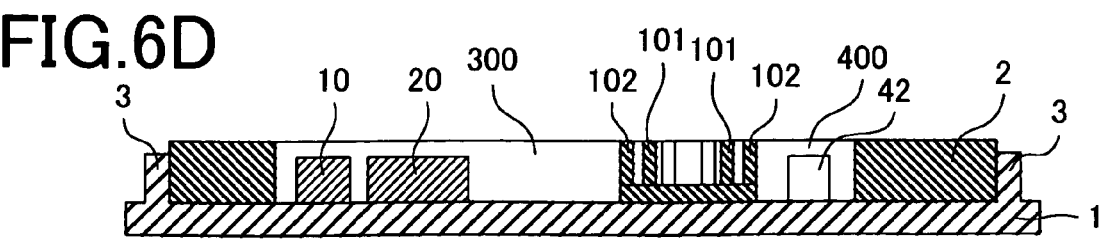

FIGS. 6A, 6B, 6C and 6D illustrate a structure of a refractive index sensor according to a first embodiment of the present invention. FIG. 6A is a plane view of the sensor, FIG. 6B is a cross-sectional view taken along the direction of arrows A-A in FIG. 6A, FIG. 6C is a cross-sectional view taken along the direction of arrows B-B in FIG. 6A, and FIG. 6D is a cross-sectional view taken along the direction of arrows C-C in FIG. 6A.

Figure 1A:
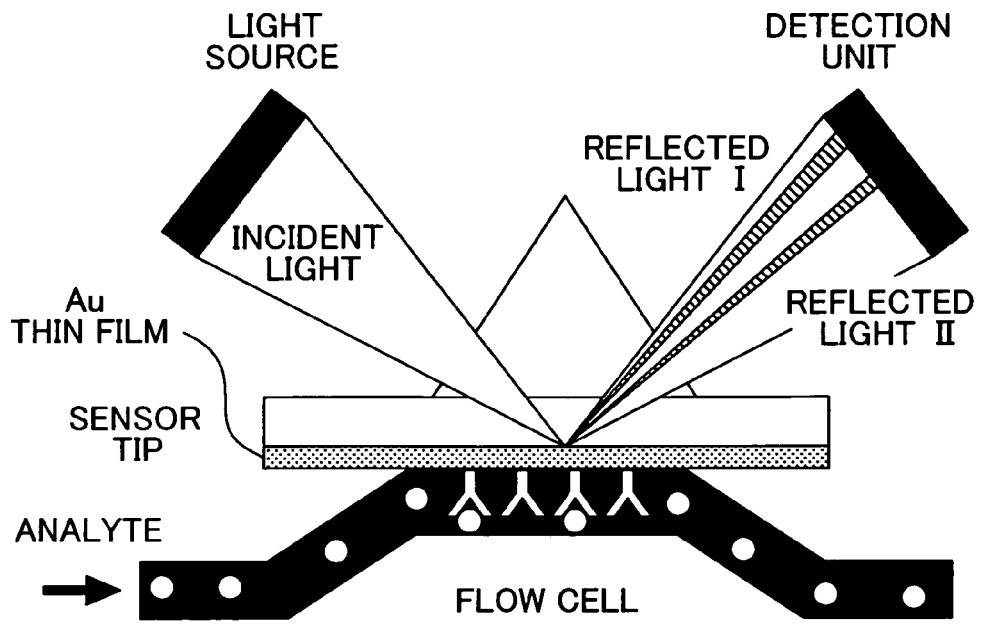
FIGS. 1A to 1C are conceptual diagrams illustrating a sensor using a surface plasmon therein.
Figure 1B:
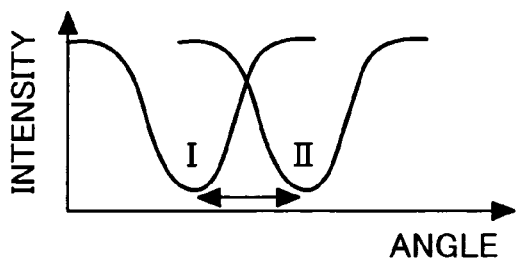
Figure 1C:
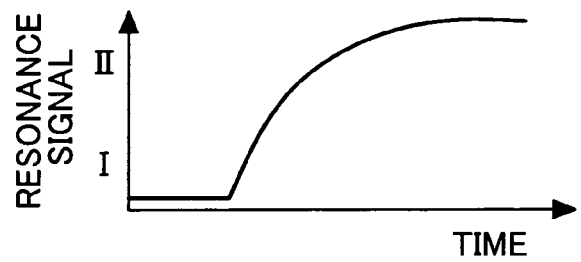
Figure 2:
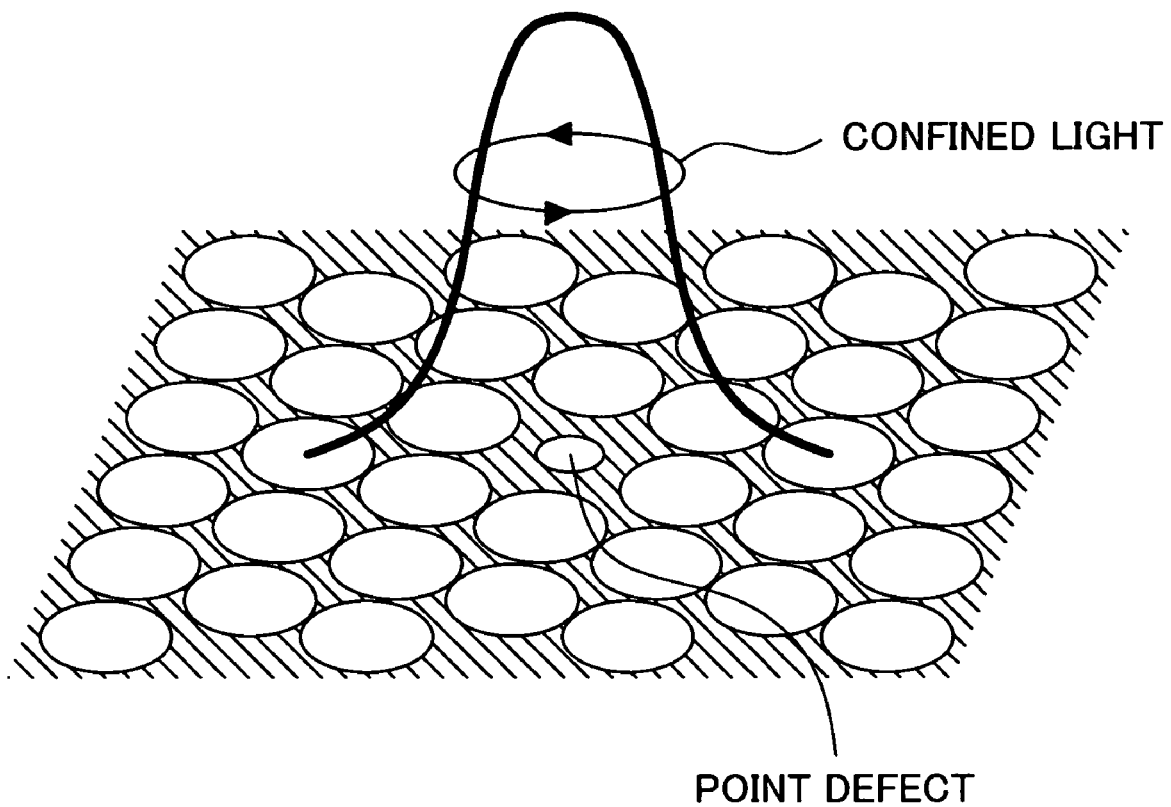
FIG. 2 is a conceptual diagram illustrating a state in which light is entrapped in a defect in a photonic crystal, provide a microcavity.
Figure 3:
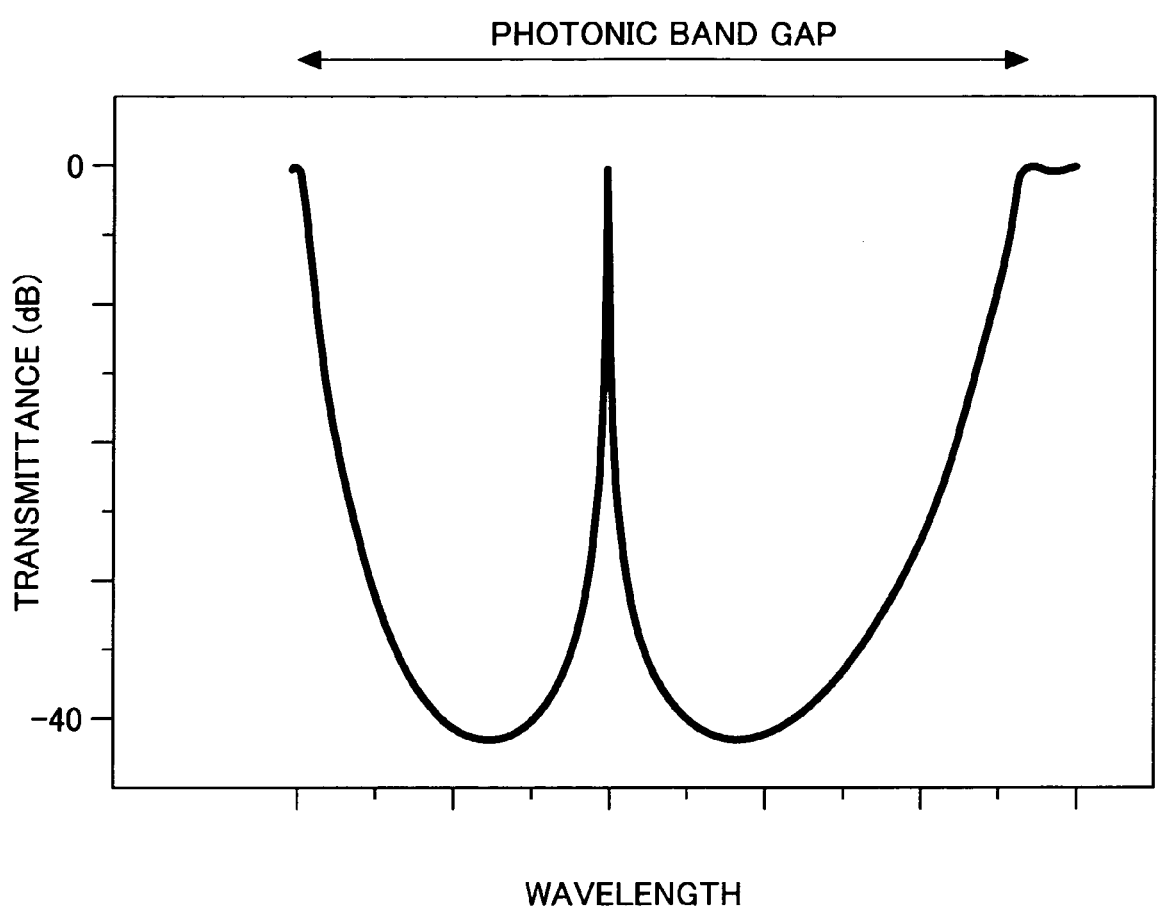
FIG. 3 is a graph illustrating a light transmission spectrum provided by the photonic crystal having a defect (s)
Figure 4:
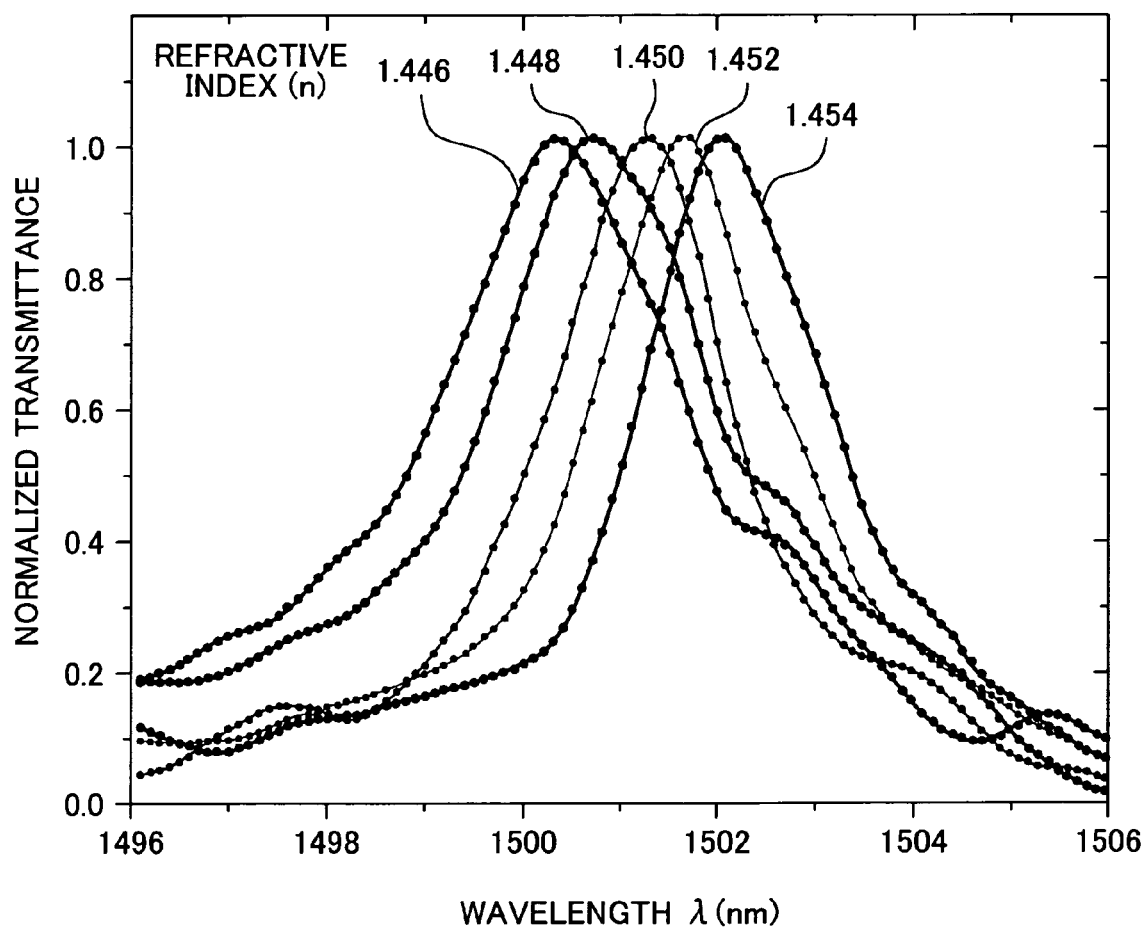
FIG. 4 is a graph illustrating the relationship between a peak of the wavelength of light from a two-dimensional photonic crystal microcavity and the refractive indexes of filled liquid.
Figure 5A:
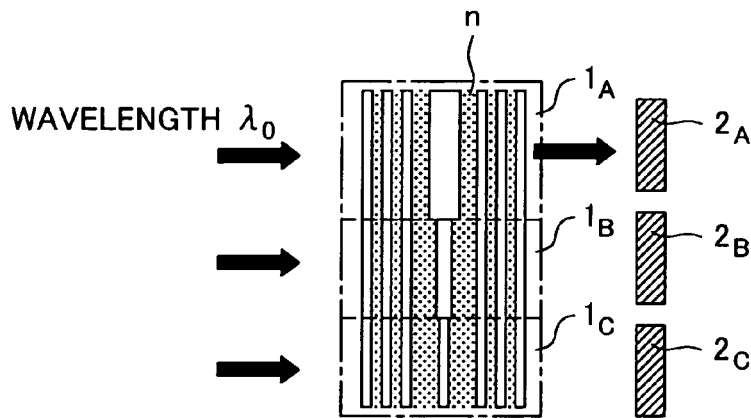
FIGS. 5A to 5C illustrate a principle of measurement of a refractive index with the micro sensor device according to the present invention.

In FIG. 6A, designated at reference numeral 1 is a substrate. Reference numeral 2 denotes a sample cell formed from a Si substrate through semiconductor processes to have a one-dimensional photonic crystal section 100 and a sample introductory section 200. The sample cell 2 can be fixed on a top surface of the substrate 1 keeping a predetermined positional relationship with the substrate 1 by means of stoppers 3 provided on an external circumferential surface of the substrate 1. After completion of measurement, the sample cell 2 can be unfixed and discarded. In the sample cell 2, the one-dimensional photonic crystal section 100 and the sample introductory section 200 are connected to each other at their bottoms on the Si substrate of the sample cell 2. The one-dimensional photonic crystal section 100 is formed with thin plates 101 and 102 as illustrated in FIG. 5A to have inside intervals therebetween different from each other from place to place. In other words, four different defective structures are provided in this case. The one-dimensional photonic crystal microcavities 31, 32, 33 and 34 are configured to have different characteristics according to their defective structures, respectively. The sample cell 2 has opening sections 300 and 400. The opening section 300 includes, on the substrate 1, a semiconductor laser 10 having an oscillation wavelength 1400 nm and a waveguide 20 dividing the outgoing light from the semiconductor laser 10 into four portions and guiding the divided light into a corresponding one of the four one-dimensional photonic crystal microcavities 31, 32, 33 and 34. The opening section 400 includes photo diodes 41, 42, 43 and 44 formed on the substrate 1 and being equivalent to the photo detector devices $2_A$, $2_B$ and $2_C$ shown in FIG. 5A. The photo diodes 41, 42, 43 and 44 correspond to the one-dimensional photo crystal microcavities 31, 32, 33 and 34, respectively.

Since FIG. 6B is a cross-sectional view taken along line A-A in FIG. 6A, only an end face of the sample introductory section 200 and those of the two thin plates 101 are shown. It is understood from FIG. 6B that the sample cell 2 is placed on a top surface of the substrate 1 and relative positions of the sample cell 2 and the substrate 1 are kept with the stoppers 3.

Since FIG. 6C is a cross-sectional view taken along line B-B in FIG. 6A, an end face of the sample introductory section 200 is not shown. A portion of a cross section of the waveguides 20 are shown in the opening section 300, and also cross sections of the thin plates 101 and 102 of the one-dimensional photonic crystal section 100 are shown. Side faces of other thin plates 101 located farther than the thin plates 101 described above are shown between the thin plates 101. In addition, a cross section of the photo diode 44 is shown in the opening section 400. It is understood from FIG. 6C that the opening sections 300 and 400 of the sample cell 2 are through-holes and the waveguide 20 and the photo diode 44 are placed in the opening section 300 and in the opening section 400 on the upper surface of the substrate 1 respectively. An end face of the stopper 3 is also shown.

Since FIG. 6D is a cross-sectional view taken along line C-C in FIG. 6A, an end face of the sample introductory section 200 is not shown. A portion of a cross section of the semiconductor laser 10 and that of the waveguide 20 are shown in the opening section 300, and also cross sections of the thin plates 101 and 102 of the one-dimensional photonic crystal section 100 are shown. Side faces of other thin plates 101 located at farther positions are shown between the thin plates 101 described above. In addition, an end face of the photo diode 43 is shown in the opening section 400. It is understood from FIG. 6D that the opening sections 300 and 400 of the sample cell 20 are through-holes, the semiconductor laser 10 and the waveguide 20 are provided at the opening 300 and the photodiode 42 is provided at the opening 400 on the upper surface of the substrate 1. In addition, end faces of the stoppers 3 are shown at this position.

Figure 5B:
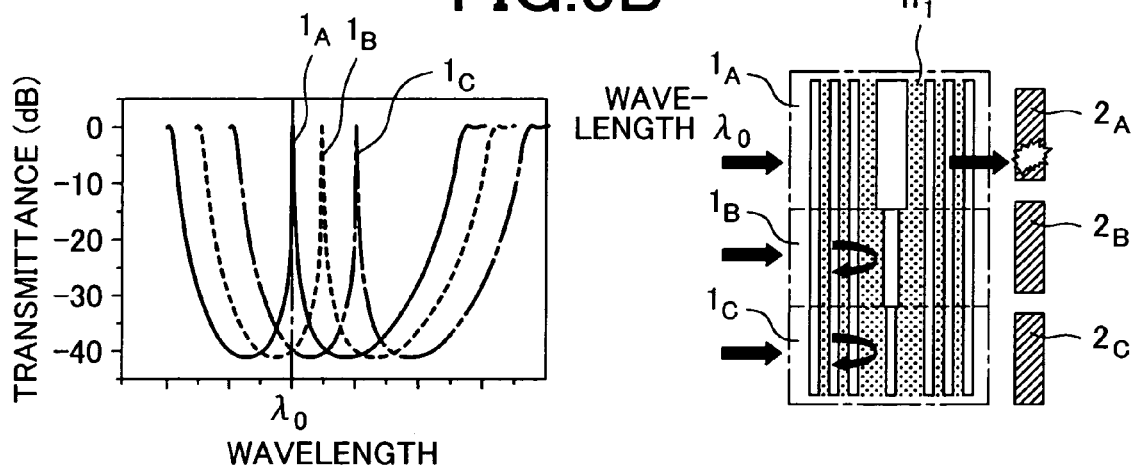
Figure 5C:
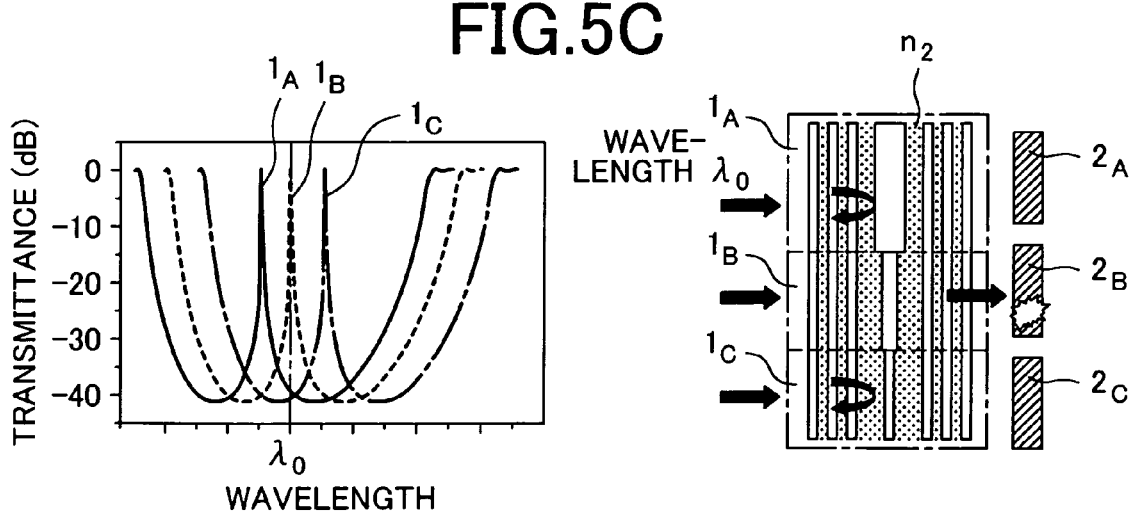

When the refractive index sensor according to the first embodiment of the present invention described with reference to FIGS. 6A, 6B, 6C and 6D is used, a sample to be measured is dropped in the sample sensor 200. The dropped sample flows toward the one-dimensional photonic crystal section 100, and then flows into between the thin plates 101 and 102 because of the capillary phenomenon. As a result, as described with reference to FIG. 5, light directed to the one-dimensional photonic crystal section 100 via the semiconductor laser 10 and the waveguide 20 is detected by any one of the one-dimensional photonic crystal microcavities 31, 32, 33 and 34 corresponding to a refractive index of the sample to be measured as well as by a corresponding one of the photo diodes 41, 42, 43 and 44. The sample to be measured is dropped into the sample introductory section 200, because the size of the one-dimensional photonic crystal section 100 is small, so that when directly dropped into the microcavities due, the sample liquid may overflows from the one-dimensional photonic crystal section 100 to contaminate the peripheral areas. Although a capacity of the sample introductory section 200 is as small as possible to enable measurement with an extremely minute amount of a sample, it is necessary to take into consideration a structure of a dropper for dropping a sample and a mechanism for dropping.

As understood by referring to FIGS. 6A, 6B, 6C and 6D, in the first embodiment of the present invention, a sample to be measured is only introduced into the sample introductory section 200 and one-dimensional photonic crystal section 100 of the sample cell 2. Therefore, after measurement for one sample to be measured is completed, a secondary sample to be measured can be measured immediately by taking off the sample cell 2 from the substrate 1 and then a new sample cell 2 is mounted onto the substrate 1.

Figure 7:
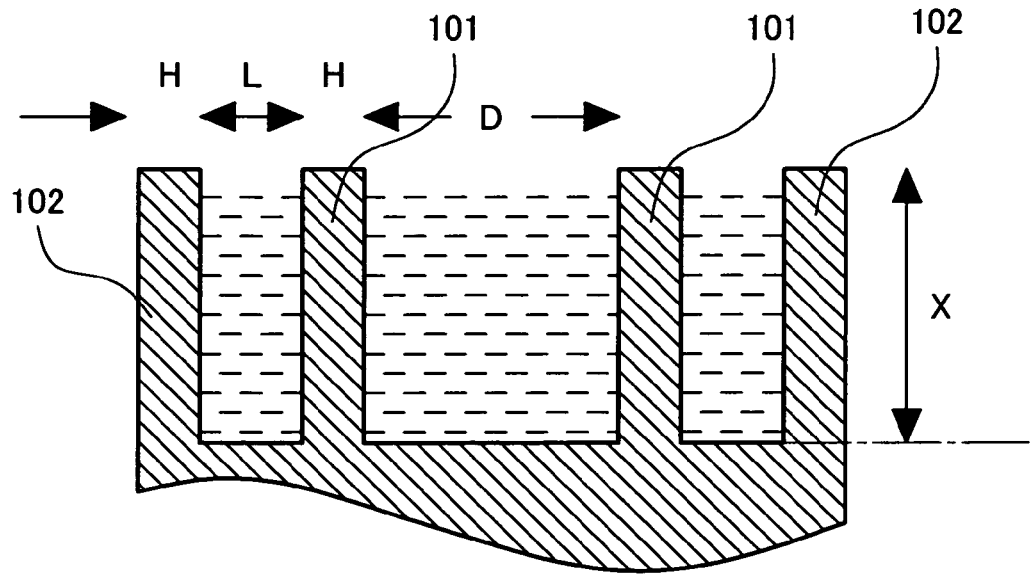
FIG. 7 is a diagram illustrating a cross-sectional structure of a one-dimensional photonic crystal according to the first embodiment.

FIG. 7 illustrates a detailed configurational example of a defect structure portion, i.e., a microcavity of the one-dimensional photonic crystal in order to detail its detecting operation. A thickness of each of the thin plates 101 and 102 is denoted by sign H, which is common to the whole one-dimensional photonic crystal section 100 (the microcavities 31 to 34), that is, H is 300 nm. A distance between the thin plates 101 and 102 is denoted by sign L, which is also common to the whole one-dimensional photonic crystal section 100 (the microcavities 31 to 34), that is, L is 777.8 nm. A distance between the thin plates 101 is denoted by sign D, which represents a width of a defective portion of the one-dimensional photonic crystal section 100. Each width varies depending on the one-dimensional photonic crystal microcavities. The microcavities 31, 32, 33 and 34 have widths of 1540 nm, 1555 nm, 1570 nm and 1585 nm, respectively. A height of the one-dimensional photonic crystal section 100 is denoted by sign X, which is 10 µm.

A process for producing a structure of the one-dimensional photonic crystal microcavities illustrated in FIG. 6 is described before explanation of a detecting operation by the microcavities. At first, a $SiO_2$ film having a thickness of 500 nm is formed by sputtering on a Si substrate. Then, a positive resist (ZEP-520) film is formed on the $SiO_2$ film, and the opening sections 300 and 400 are patterned by electron beam drawing. Next, the $SiO_2$ film is etched with Ar and $C_4F_8$. After the resists are incinerated with thermal $UVO_3$ for exfoliation, a through-hole is formed by dry etching the Si substrate using $SF_6$ and $O_2$. The openings 300 and 400 are formed as described above. Next, negative resist (SAL601-SR7) film is provided on the $SiO_2$ film and the sample cell 2 is patterned by electron beam drawing. Then, the $SiO_2$ substrate is etched with Ar and $C_4F_8$. After the resists are incinerated with thermal $UVO_3$ for exfoliation, high aspect ratio ICP dry etching is performed on the Si substrate using $SF_6$ and $O_2$. In this step, a bottom electrode is cooled down to $-100°$ C. or below with liquid nitrogen. The one-dimensional photonic crystal microcavities are produced as described above.

On the other hand, a Si substrate is prepared for the substrate 1, and then a film for the waveguide 20 is produced by using polymer at a position corresponding to the opening section 300 of the sample cell 2. Specifically, a polyimide film is prepared by spin-coating polyimide. A thickness of the polyimide film is 5 µm. Then, the waveguides 20 is formed by photolithography and etched using the dry-etching technique. Also the stopper 3 is formed along with the above processes. In succession, the semiconductor laser 10 corresponding to the shape of the waveguides is mounted at a position corresponding to the opening section 300. Finally, at a position corresponding to the opening 400, a photo diode array including the photo diodes 31, 32, 33 and 34 associated with the defective portions is mounted on the substrate.

In an operating demonstration, as illustrated in FIG. 7, liquid as a material to be measured was filled into spacing of the Si structure and measured. This time, the material used for the measurement is a mixture of water and ethanol.

Figure 8:
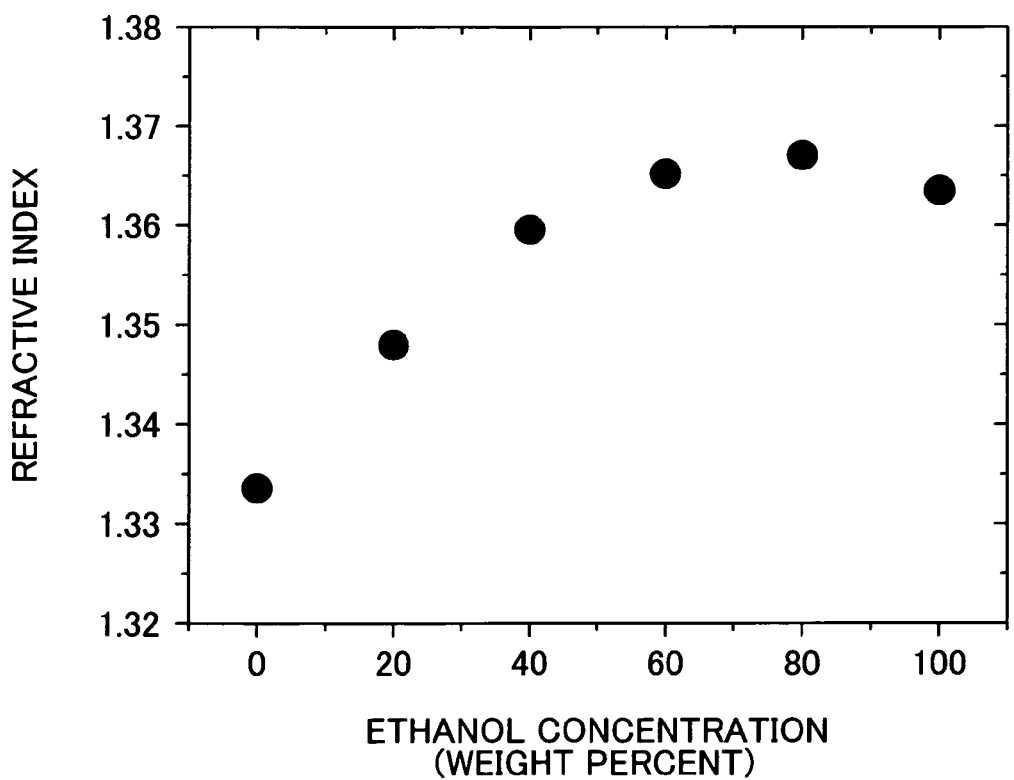
FIG. 8 is a graph illustrating the relationship between ethanol concentration (weight percent) of a water-ethanol mixture liquid and a refractive index of the mixture liquid.

FIG. 8 is a graph illustrating the relationship between a refractive index and ethanol concentration (weight percent) of a water-ethanol mixture at a temperature of 15° C. The data used herein is described in A Manual for Chemistry (Basic) (Handbook for Chemistry (Basic version)); 3rd edition; page 2; Chemical Society in Japan. In this document, it is described that the refractive index of the mixture varies within a range of 1333 to 1367 depending on the ethanol concentration (weight ratio).

Figure 9:
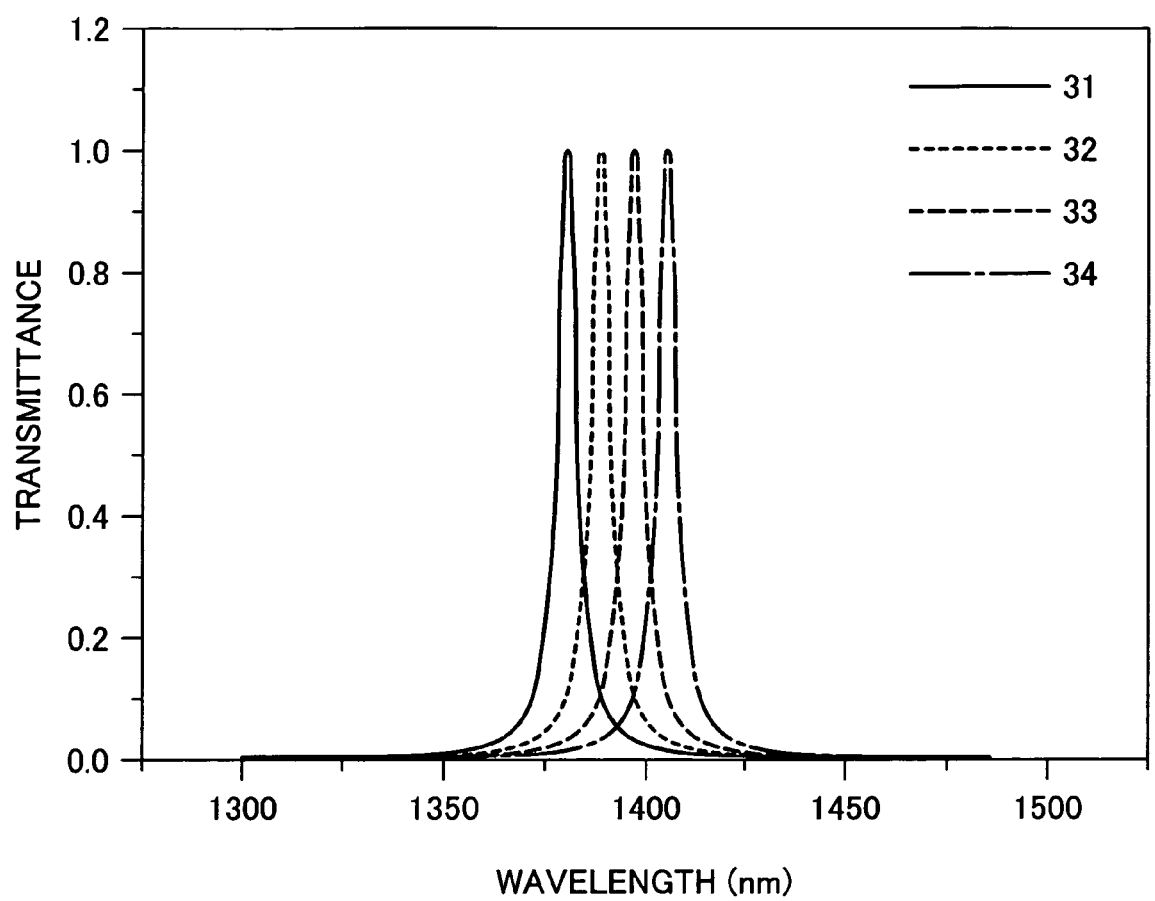
FIG. 9 is a graph illustrating transmission spectrums provided by the one-dimensional photonic crystal microcavities 31 to 34 in the first embodiment.

FIG. 9 shows that widths of the defect portions D of the one-dimensional photonic crystal microcavities are 1540 nm, 1555 nm, 1570 nm and 1585 nm when the refractive index of the mixed liquid is 1,335, that is, shows the transmission spectrums of the one-dimensional photonic crystal microcavities 31, 32, 33 and 34. The wavelengths of the transmission spectrums are shifted with each other depending on the difference of the defective portion D. A distance between peaks is designed to be about a half value width.

Figure 10:
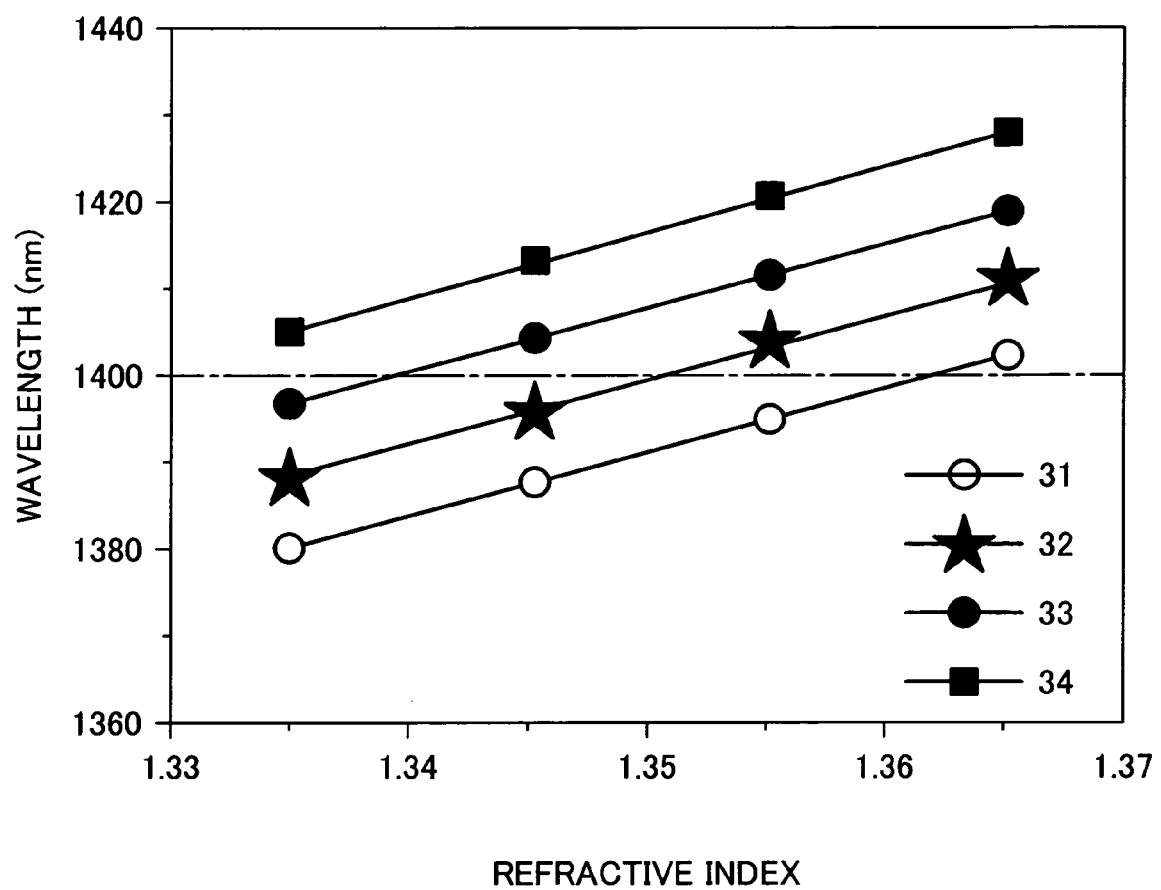
FIG. 10 is a graph illustrating the relationship between the peak wavelengths in transmission spectrums provided by the one-dimensional photonic crystal microcavities 31 to 34 in the first embodiment and a refractive index of liquid filled therein.

FIG. 10 illustrates the relationship between peak wavelengths of the transmission spectrums of the one-dimensional photonic crystal microcavities 31, 32, 33 and 34 and the refractive index of the mixture. It indicates that the peak wavelengths substantially linearly increase with an increase in refractive index.

Operations in the first embodiment are described with reference to FIGS. 8, 9, and 10. Light emitted from the semiconductor laser 10 is equally divided into four pieces of light through the waveguides 20. The divided pieces of light are each directed to a corresponding one of the one-dimensional photonic crystal microcavities 31, 32, 33 and 34. Spaces in the microcavities are filled with the water-ethanol mixture. FIG. 8 shows that when a concentration of the ethanol is 10%, a refractive index of the mixture is 1.34. In FIG. 10, a wavelength 1400 nm of incident light is indicated by a dashed line, and the light passes through at an intersection point of the dashed line and solid lines. It is understood from FIG. 10 that, when the refractive index of the mixture is 1.34, the light passes through the one-dimensional photonic crystal microcavity 33. Therefore, only the photo diode 43 can detect signals, that is, the photo diodes 41, 42 and 44 do not detect the light.

Figure 11:
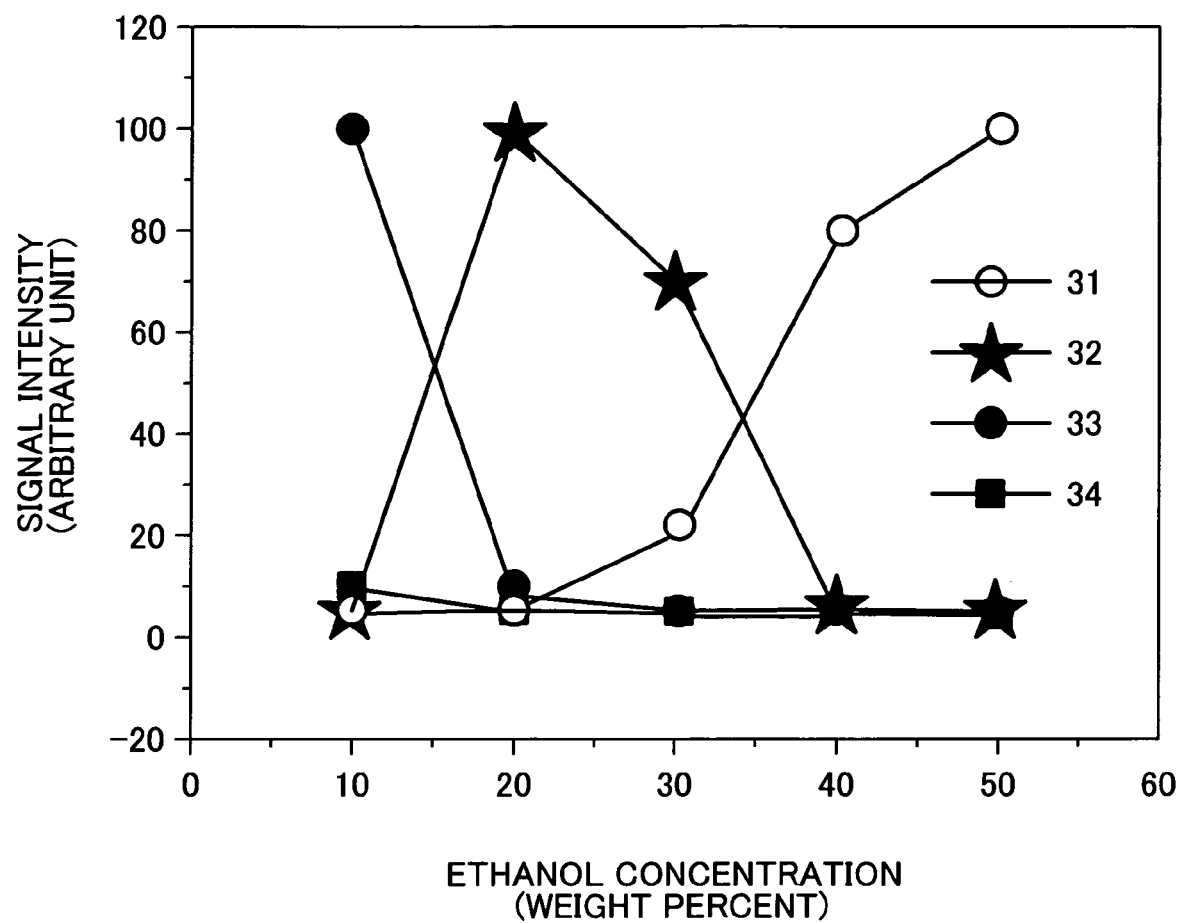
FIG. 11 is a graph illustrating the relationship between concentration of a mixture liquid and outputs of four photodiodes in the first embodiment.

FIG. 11 illustrates outputs from the photo diodes 41, 42, 43 and 44 when a concentration of ethanol is changed on a 10%-basis in the range from 10% to 50%. A horizontal axis in FIG. 11 indicates ethanol concentration and a vertical axis indicates detection outputs of the photo diodes 41, 42, 43 and 44. It is confirmed that the detection outputs of the photo diodes 41, 42, 43 and 44 change in response to a change of a refractive index caused by a change of ethanol concentration, whereby changes of the refractive index can be detected. It is also confirmed that, even when any one of the peaks of the photonic crystal does not coincide exactly with 1400 nm for e.g. 30% or 40% of the concentration, since a certain amount of light passes through the microcavity because of extension of a line width of transmission spectrum peaks, a refractive index can be measured by comparing intensities of transmitted light with each other. This is probably because a distance between peaks of the transmission spectrums is about a half value width.

Second Embodiment

In a second embodiment of the present invention, a two-dimensional photonic crystal, instead of the one-dimensional photonic crystal, is used as the photonic crystal section 100.

Figure 12A:
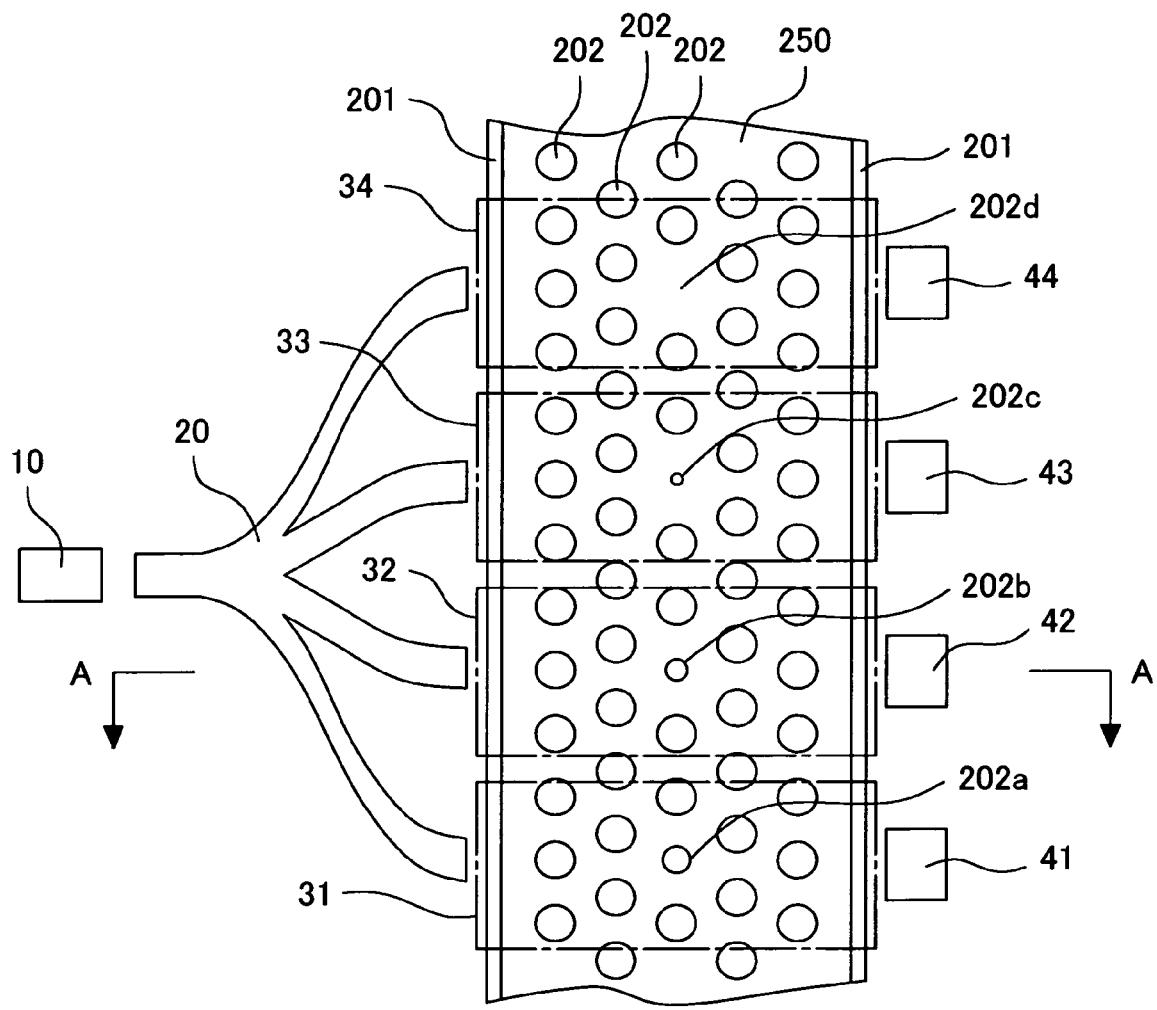
FIGS. 12A and 12B illustrate a second embodiment of the present invention in which a micro sensor device is built with a two-dimensional photonic crystal.
Figure 12B:
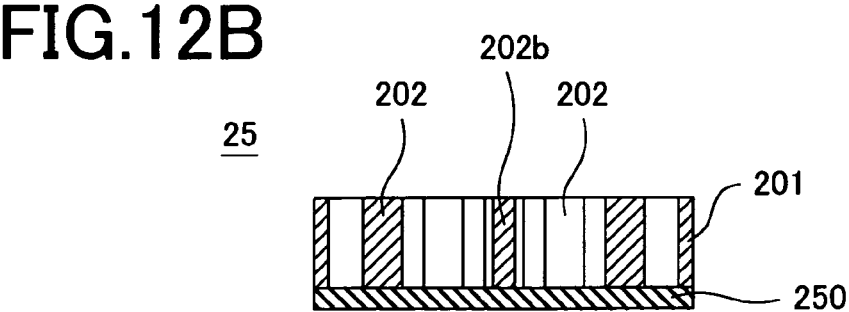

A two-dimensional photonic crystal 25 in the second embodiment is mainly composed of a Si layer with a thickness of 200 nm and a SIO substrate configured of a $SiO_2$ layer with a thickness of 1 µm. FIG. 12A is a plan view illustrating the two-dimensional photonic crystal 25, and FIG. 12B is a cross-sectional view illustrating the two-dimensional photonic crystal 25 taken along line A-A in FIG. 12A. Reference 250 denotes the $SiO_2$ layer, and side walls 201 of a sample flow path are formed on both side faces of the Si layer on the SiO₂ layer. Columns 202 each having a diameter of 250 nm are provided in triangular form between the side walls 201 to form a photonic crystal. A distance between centers of adjacent columns 202 (a lattice constant) is 400 nm. Point defects are introduced by making the diameters of the columns 202a, 202b, 202c, and 202d smaller. The diameters of the columns 202a, 202b, and 202c are 150 nm, 100 nm, and 50 nm, respectively, and the column 202d is lacked. A thickness of the two-dimensional photonic crystal 25 is as substantially small as 200 nm, and also a coupler 21 is made of Si. The size of a waveguide of the coupler is 200 nm×200 nm. In FIG. 12, the semiconductor layer 10 and the waveguide 20, photonic microcavities 31, 32, 33 and 34, and the photodiodes 41, 42, 43, and 44 are shown as in FIG. 6. The configuration shown in FIG. 12 is substantially the same as that described in the first embodiment excluding the point that the two-dimensional photonic crystal is used in place of the one-dimensional photonic crystal.

Third Embodiment

Figure 13A:
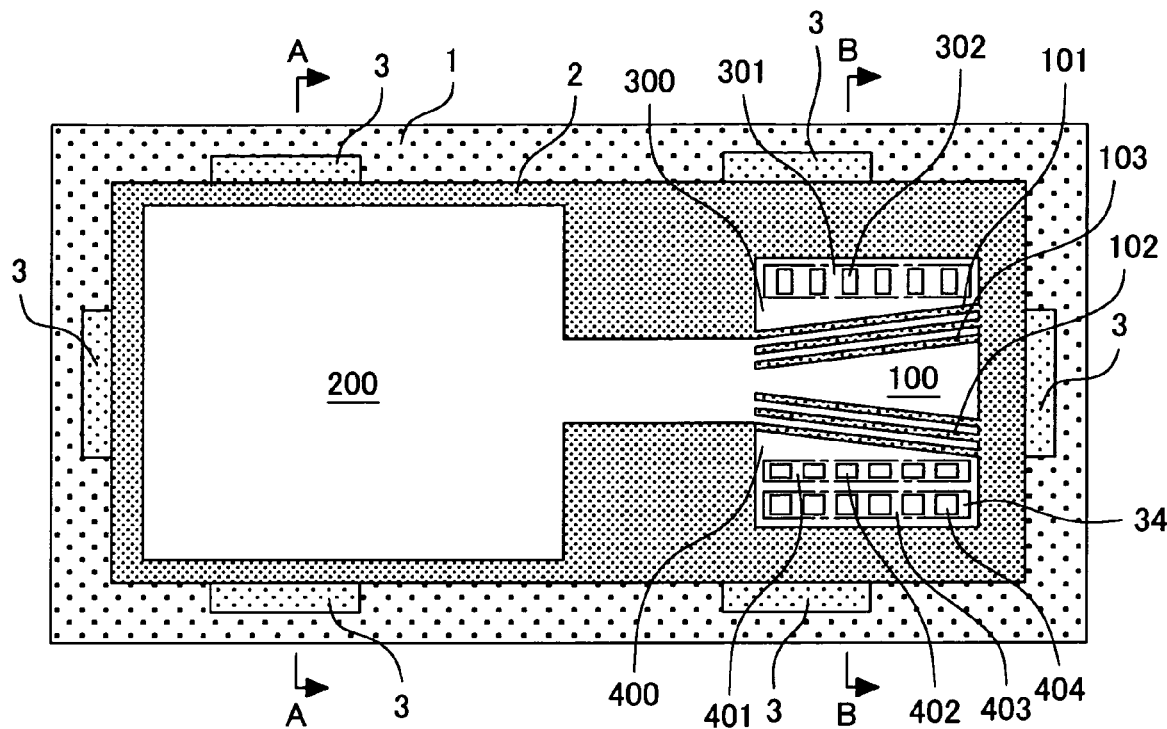
FIG. 13 illustrates a third embodiment of the present invention in which a liquid refractive index sensor is built with the micro sensor device according to the present invention.
Figure 13B:
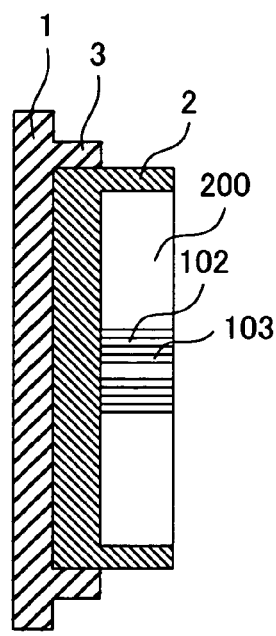
Figure 13C:
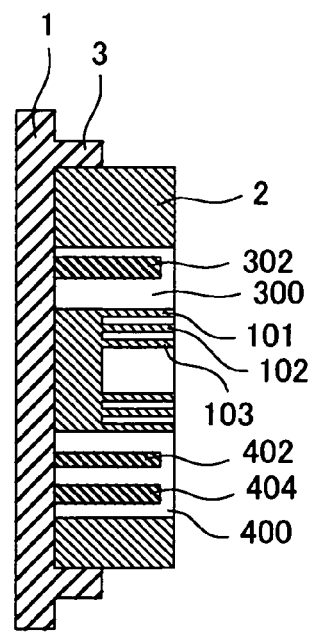

A configuration of a refractive index sensor according to a third embodiment of the present invention is shown in FIGS. 13A to 13C. FIG. 13A is a plan view of the refractive index sensor, FIG. 13B is a cross-sectional view illustrating the refractive index sensor taken along line A-A in FIG. 13A, and FIG. 13C is a cross-sectional view illustrating the refractive index sensor taken along line B-B in FIG. 13A. Also in the third embodiment, as in the first embodiment, the sample cell 2 is removably held on the substrate 1 via the stoppers 3 as guides. Provided in the sample cell 2 are a sample introductory section 200, a one-dimensional photonic crystal section 100 contiguous to the section 200, and opening sections 300 and 400. In the third embodiment, the one-dimensional photonic crystal section 100 provided in the sample cell 2 is formed with linear thin plates 101, 102, and 103. The thin plates 101, 102, and 103 are equally spaced apart from each other as in the second embodiment. However, a space between the opposite thin plates 103 varies as they go in the longitudinal direction. In the third embodiment, an LED array 301 composed of a plurality of LEDs 302 arranged at predetermined intervals is provided in the opening section 300 in place of the semiconductor laser 10 and the waveguide 20 used in the first embodiment. Furthermore, provided in the opening section 400 are a lens array 401 in which a plurality of lenses 402 are arrayed at predetermined intervals and a photodiode array in which a plurality of photodiodes are arrayed at predetermined intervals are used in place of the photodiodes 41, 42, 43, and 44 used in the first embodiment. Needless to say, the interval between the adjacent LEDs 302, the interval between the adjacent lenses 402, the interval between the adjacent LEDs 302, and the interval between the adjacent photodiodes are equal to one another.

In the first and second embodiments, the semiconductor laser 10 and the waveguide 20 are used to split light from one light source and supply the split light to photonic crystal microcavities. In the third embodiment, the LEDs 302 each emitting light with the same wavelength are arranged in array and used as a light source. Action of the one-dimensional photonic crystal is the same as that described in the first embodiment. However, in the configuration according to the first embodiment, elements each having a different defect width are coupled to each other in the first embodiment, whereas a width of a defect section continuously varies in a direction perpendicular to a light-passing direction.

Also in the third embodiment, a sample to be measured is dropped into the sample introductory section 200 of the sample cell 2. The sample flows into the one-dimensional photonic crystal section 100 because of the capillary phenomenon, and the refractive index is detected by the method detailed in the first embodiment.

Fourth Embodiment

An example in which the micro sensor device according to the present invention is mounted on a microchemical chip is described in a fourth embodiment of the present invention. The microchemical chip is used in a technique for realizing various operations in chemical reactions such as mixing, transport, heating, and extracting of a sample on a chip by the MEMS technique. By realizing the operations on a chip, not only size reduction and availability of a minute amount of a sample, but also higher efficiency in chemical reactions provided by size reduction can be expected.

Figure 14:
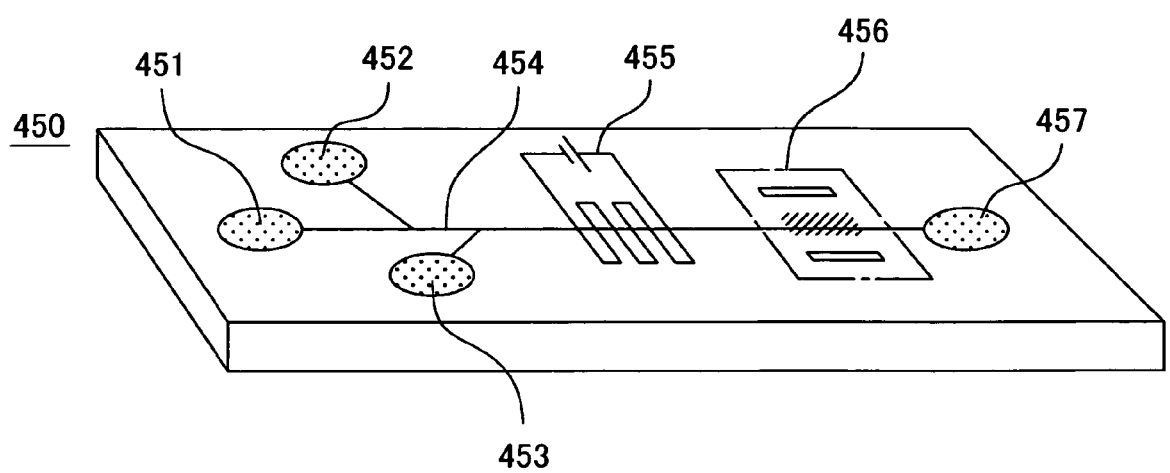
FIG. 14 illustrates a fourth embodiment of the present invention in which the micro sensor device according to the present invention is built in a microchemical chip.

As shown in FIG. 14, provided on a top surface of a microchemical chip 450 are a micro sensor device 456 of the present invention and a drain 457 in addition to a sample cell 451, reagent cells 452, 453, micro flow path 454, and a heating section 455 for promoting chemical reactions.

A sample introduced into the sample cell 451 is mixed with reagents supplied from the reagent cells 452, 453 in the heating section 455, in which the mixture is heated to promote chemical reactions. A refractive index of the reaction product is measured by the micro sensor device 456. As easily understood by referring to FIG. 6A, FIG. 12A, and FIG. 13A, it may be regarded that, in the fourth embodiment, the sample introductory section 200 shown in each of the embodiments above is replaced with the sample cell 451, the reagent cells 452, 453, the micro flow path 454, and the heating section 455 for promoting reactions in the microchemical chip 450. Therefore, it is necessary only to prepare a micro sensor device 456 in which the sample introductory section 200 and an end portion of the one-dimensional photonic crystal section 100 are cut off and to provide the micro sensor device 456 on the downstream side of the heating section 455 for promoting reactions in the microchemical chip 450. In the first to third embodiments, the sample cell in which a measure sample flows, and the light source and the sensor portion are mounted on the respective different substrates. In this case, as with the first to third embodiments, the microchemical chip 450, and a light source for the microchemical chip 450 and the sensor portion are mounted on respective different substrates. With this configuration, the microchemical chip 450 may be disposable.

In the embodiments, while descriptions are mainly made of application to biochemical measurement, applications of the micro sensor device according to the present invention are not limited to those described above. That is, the micro sensor device according to the present invention may be applied also to chemical synthesis and analysis of environmental pollutants such as endocrine disturbing chemicals or dioxin. In any case, the present invention is applicable on the condition that a sample to be measured is provided as a liquid and changes of a refractive index of the sample can be detected as information.

What is claimed is:

1. A micro sensor device for measuring a refractive index of a liquid sample to be measured, comprising:
   a combination of a cavity unit; a common light source for emitting light with a signal wavelength; and a light receiving unit, wherein said cavity unit including a plurality of cavities or an array of cavities, each cavity being responsive to a different particular resonance wavelength, each cavity being arranged in a different position and resonance wavelengths of adjacent cavities differing from each other by a predetermined amount;

wherein said resonance wavelengths of the plurality of cavities being shifted depend on a wavelength of the refractive index of the liquid sample to be measured;

wherein said light receiver unit including a plurality of light receivers or an array of light receivers, each of which is located in a position corresponding to one of said cavity, for detecting an intensity of the light with the signal wavelength from the common light source passed through said cavity, respectively, wherein each cavity includes:

a photonic crystal configured as a periodic structure such that a material having a predetermined refractive index, and a first portion having at least one liquid channel allowing for flow of the liquid sample, are repeated at a cycle of a wavelength order of the light corresponding to said resonance wavelength, wherein said photonic crystal is a one-dimensional photonic crystal; and a second portion provided in the photonic crystal and having a non-uniform element formed in the periodic structure, wherein the second portion having a varied configuration coinciding with said one of said particular resonance wavelengths according to a position respectively at which the liquid sample to be measured flows, so as to allow the light having the particular resonance wavelength to pass through a coincident cavity, wherein the micro sensor device is configured such that a refractive index of the liquid sample is detected by identifying a position of the photonic crystal where the light passes through.

2. The micro sensor device according to claim 1, wherein the plurality of cavities or the cavity array, and the common light source and the plurality of light receivers or the light receiver array, are formed on respective different substrates.

3. The micro sensor device according to claim 1, wherein each of said one-dimensional photonic crystal is made of Si with a different thickness.

4. A micro sensor device for measuring a refractive index of a liquid sample to be measured, comprising:

a combination of a cavity unit; a common light source for emitting light with a signal wavelength; and a light receiving unit, wherein said cavity unit including a plurality of cavities or an array of cavities, wherein each cavity being responsive to a different particular resonance wavelength and being arranged in a different position, and said resonance wavelengths of adjacent cavities differing from each other by a predetermined amount;

wherein said resonance wavelengths of the plurality of cavities being shifted depend on a wavelength of the refractive index of the liquid sample to be measured;

wherein each cavity including a photonic crystal configured as a periodic structure such that a material having a predetermined refractive index, and a first portion of at least one liquid channel allowing for flow of the liquid sample, are repeated at a cycle of a wavelength order of the light corresponding to said resonance wavelength, wherein said photonic crystal is a one-dimensional photonic crystal; and a second portion provided in the photonic crystal having a non-uniform element formed in the periodic structure, wherein the second portion having a varied configuration coinciding with said one of said particular resonance wavelengths according to a position respectively at which the liquid sample to be measured flows, so as to allow the light having the particular resonance wavelength pass through a coincident cavity, wherein said light receiver unit including a plurality of light receivers or an array of light receivers, each of which is located in a position corresponding to one of said cavity, respectively, for detecting an intensity of the liquid with the signal wavelength from the common light source passed through said cavity, respectively wherein the micro sensor device is configured such that a refractive index of the liquid sample is detected by identifying a position of the photonic crystal where the light passes through.

5. The micro sensor device according to claim 4, wherein the plurality of cavities or the cavity array, and the common light source and the plurality of light receivers or the light receiver array, are formed on respective different substrates.

6. The micro sensor device according to claim 4, wherein each of said one-dimensional photonic crystal is made of Si with a different thickness.

* * * * *